United States Patent
Oakley et al.

(10) Patent No.: US 9,987,433 B2
(45) Date of Patent: Jun. 5, 2018

(54) ASSEMBLY FOR A DRUG DELIVERY DEVICE AND METHOD OF OPERATING THE SAME

(71) Applicant: Sanofi, Paris (FR)

(72) Inventors: Tom Oakley, Cambridge (GB); Matt Schumann, Bourn (GB); Stuart Milne, Buckden St. Neots (GB)

(73) Assignee: Sanofi, Paris (FR)

( * ) Notice: Subject to any disclaimer, the term of this patent is extended or adjusted under 35 U.S.C. 154(b) by 241 days.

(21) Appl. No.: 14/905,446

(22) PCT Filed: Jul. 17, 2014

(86) PCT No.: PCT/EP2014/065335
§ 371 (c)(1),
(2) Date: Jan. 15, 2016

(87) PCT Pub. No.: WO2015/007816
PCT Pub. Date: Jan. 22, 2015

(65) Prior Publication Data
US 2016/0158455 A1 Jun. 9, 2016

(30) Foreign Application Priority Data

Jul. 17, 2013 (EP) .................................... 13176861

(51) Int. Cl.
*A61M 5/315* (2006.01)
*A61M 5/20* (2006.01)
*A61M 5/31* (2006.01)

(52) U.S. Cl.
CPC .......... *A61M 5/31541* (2013.01); *A61M 5/20* (2013.01); *A61M 5/3146* (2013.01);
(Continued)

(58) Field of Classification Search
CPC ............ A61M 5/31541; A61M 5/3146; A61M 5/31573; A61M 5/31501; A61M 5/31535;
(Continued)

(56) References Cited

U.S. PATENT DOCUMENTS 5,383,865 A 1/1995 Michel
7,699,815 B2 4/2010 Langley et al.

FOREIGN PATENT DOCUMENTS

WO WO 2006/089734 8/2006
WO WO 2007/066152 6/2007
(Continued)

OTHER PUBLICATIONS

Rote Liste, "50. Hypophysen-, Hypothalamushormone, andere regulatorische Peptide u. ihre Hemmstoffe,"Chapter 50, ed. 2008, 20 pages.
(Continued)

*Primary Examiner* — Manuel Mendez
(74) *Attorney, Agent, or Firm* — Fish & Richardson P.C.

(57) ABSTRACT

An assembly for a drug delivery device (200) is presented which comprises a housing (24) having a proximal end (25) and a distal end (26), a cartridge, a plunger (19) which is movably retained in the cartridge (14) and a piston rod (6). The assembly further comprises a rod displacement feature (33). The assembly is configured such that, in an initial state of the assembly, the piston rod (6) and the rod displacement feature (33) are arranged such that movement of the rod displacement feature (33) from the first position to the second position is transferred to the piston rod (6) such that the piston rod (6) is moved with respect to the cartridge (14) and the assembly is switched from the initial state to a primed state. In the primed state, movement of the rod displacement feature (33) from the first position to the second position is not transferred to the piston rod (6).

16 Claims, 7 Drawing Sheets (52) U.S. Cl.
CPC ....... *A61M 5/31573* (2013.01); *A61M 5/3157* (2013.01); *A61M 5/31501* (2013.01); *A61M 5/31535* (2013.01); *A61M 5/31543* (2013.01); *A61M 5/31553* (2013.01); *A61M 5/31561* (2013.01); *A61M 5/31583* (2013.01); *A61M 2005/3126* (2013.01); *A61M 2205/581* (2013.01); *A61M 2205/586* (2013.01)

(58) Field of Classification Search
CPC .......... A61M 5/31543; A61M 5/31553; A61M 5/31561; A61M 5/3157; A61M 5/31583
USPC ........................ 604/207, 134, 135, 136, 137
See application file for complete search history.

(56) References Cited

FOREIGN PATENT DOCUMENTS

| WO | WO 2009/147112 | 12/2009 |
| WO | WO 2011/063842 | 6/2011 |

OTHER PUBLICATIONS

International Search Report and Written Opinion in International Application No. PCT/EP2014/065335, dated Oct. 2, 2014, 11 pages.
International Preliminary Report on Patentability in International Application No. PCT/EP2014/065335, dated Jan. 19, 2016, 9 pages.

ASSEMBLY FOR A DRUG DELIVERY DEVICE AND METHOD OF OPERATING THE SAME

CROSS-REFERENCE TO RELATED APPLICATIONS

This application is a U.S. national stage application under 35 USC § 371 of International Application No. PCT/EP2014/065335, filed on Jul. 17, 2014, which claims priority to European Patent Application No. 13176861.6, filed on Jul. 17, 2013, the entire contents of which are incorporated herein by reference.

The present disclosure relates to an assembly for a drug delivery device, e.g. an injector-type device such as a pen-type device and a method of operating the same.

Drug delivery devices are, for example, known from U.S. Pat. No. 5,383,865 A, U.S. Pat. No. 7,699,815 B2 and WO 2006/089734 A1. It is an object of the present disclosure to provide an assembly for a drug delivery device which facilitates priming of the drug delivery device and to provide an associated method of operating the assembly.

This object is achieved by the subject-matter of the independent claims. Advantageous embodiments and refinements are subject-matter of the dependent claims.

One aspect of the present disclosure relates to an assembly for a drug delivery device comprising a housing having a proximal end and a distal end. The assembly further comprises a cartridge, a plunger being movably retained in the cartridge and a piston rod which is arranged to move the plunger distally with respect to the cartridge. The cartridge may contain a drug. The assembly further comprises a rod displacement feature which is movable between a first and a second position with respect to the housing. The assembly is configured such that, in an initial state of the assembly, the piston rod and the rod displacement feature are arranged such that movement of the rod displacement feature from the first position to the second position is transferred to the piston rod such that the piston rod is moved with respect to the cartridge and the assembly is switched from the initial state to a primed state. This embodiment enables the transfer of a force which may be applied by a user of the assembly via the rod displacement feature to the piston rod with respect to the cartridge such that the assembly is switched from the initial state to the primed state.

In an embodiment, the direction of movement of the rod displacement feature from the first to the second position is the distal direction. This embodiment allows for an expedient arrangement or design of the assembly, wherein the advantages mentioned in the present disclosure can be exploited easiest.

The assembly may form part of a drug delivery device. Alternatively, the assembly may be a drug delivery device. Preferably, the drug delivery device comprises the assembly, whereby a priming of the drug delivery device is enabled or facilitated. The initial state may be an as-fabricated state or an as-assembled state of the assembly. Preferably, in the initial state a user of the assembly has not yet carried out any actions concerning a function or preparation of the assembly. Particularly, the piston has not yet been moved such that a full initial dose of drug may be retained in the cartridge. In this state, there may be a considerable static friction between the plunger and the cartridge which originates from the manufacturing of the cartridge and/or storage of the plunger within the cartridge. Usually, such cartridges retaining a plunger are preassembled and mounted to further components of the assembly or a drug delivery device in a later step.

Preferably, the priming is carried out by the user of the assembly, e.g. via a dose button. Before the assembly has been primed, the user may already have set a dose of the drug delivery device or not. If the user has already set a dose, said dose or a corresponding dose may be dispensed by the drug delivery device when the drug delivery device is primed.

In an embodiment, in the primed state, movement of the rod displacement feature from the first position to the second position is not transferred to the piston rod. In other words, the rod displacement feature moves without interacting with the piston rod. The second position may exhibit a defined end position, wherein no further movement is possible. This embodiment provides the advantage that, when the assembly is primed such that movement of the rod displacement feature from the first to the second position has been transferred to the piston rod, said movement of the piston rod with respect to the cartridge does not occur during a subsequent movement of the rod displacement feature from the first position to the second position. In other words, priming essentially relates to an initial or first movement of the piston rod with respect to the cartridge. The assembly may be configured such that the piston rod interacts with the plunger during movement of the piston rod from the first position to the second position. Preferably, said priming may be carried out by a user of the assembly, via an actuation of further components of the assembly.

As the plunger is moved with respect to the cartridge during priming, a predetermined dose, e.g. a dose of drug such as a priming dose, may be dispensed from the drug delivery device during priming. Said dose may correspond to the distance the plunger is moved with respect to the cartridge.

In an embodiment, when the assembly is switched from the initial state to the primed state, the plunger is moved with respect to the cartridge and an initial static friction force between the plunger and the cartridge is overcome by the movement of the rod displacement feature from the first to the second position. As an advantage of this embodiment, any further movement of the plunger within the cartridge, e.g. during a dispensing operation of the drug delivery device may be carried out with less effort, as the initial static friction force has already been overcome.

In an embodiment, the assembly comprises a drive mechanism which is configured to transfer a driving force to the piston rod in the primed state. With the aid of the drive mechanism, the piston rod may be further moved, preferably in the distal direction, such that also the plunger is moved distally with respect to the cartridge, e.g. in order to dispense a dose of drug from the drug delivery device. The drive mechanism may be configured to drive the piston rod according to a set dose.

In an embodiment, the force required to move the plunger relative to the cartridge in the initial state, is the sum of the initial static friction force and the force necessary to push away or displace the liquid of drug from the cartridge. Said force is, expediently, greater than the driving force. Preferably, the initial static friction force is, in particular, also greater than the driving force.

In an embodiment, the initial static friction force is greater than the driving force. A minimum and a maximum driving force may be exertable by the drive mechanism. Furthermore, the driving force may take values from a range between the minimum and a maximum driving force. This provides the advantage that the drive mechanism may be designed to apply comparatively small forces to the piston rod, whereby a cost-effective and space-saving assembly is achieved. A further advantage relates to the fact that by a moderate force which is applied by the drive mechanism, further components or mechanisms of the assembly which require to overcome or temporarily to overcome the said force during an operation of the assembly may be configured simpler, cheaper and/or space-saving.

In an embodiment, the rod displacement feature is comprised by a displacement member of the drive mechanism, wherein the displacement member is movable to selectively couple a drive member to the piston rod in order to transfer the driving force to the piston rod. According to this embodiment, the assembly may be designed with a comparable low number of interacting parts, as said displacement member provides for the feature of the rod displacement feature, whereby the displacement member is also involved in a coupling to the piston rod via the drive member which may be required by the assembly to function properly.

In an embodiment the assembly comprises a spring element which is arranged and configured such that movement of the rod displacement feature from the first to the second position loads or biases the spring element and the spring force of the spring element tends to move the rod displacement feature back into the first position. Thereby, it may be achieved that after the rod displacement feature has been moved to the second position, it may be automatically repulsed by the spring force of the spring element such that, e.g. the user of the assembly may again operate the assembly.

In an embodiment, the assembly comprises a drive spring which is arranged and configured to drive the movement of the piston rod via the drive member by a driving force provided by a drive spring, whereby the driving force provided by the drive spring is exerted on the piston rod. The drive spring may be a torsion spring. During a setting operation of the drug delivery device, the drive spring may be loaded, and during a dispensing operation of the drug delivery device, the spring energy of the biased drive spring may be used to drive the piston rod.

In an embodiment, the assembly comprises a dose button being arranged and configured such that movement of the dose button with respect to the housing initiates a delivery of a dose of drug. Said movement, preferably being a distal movement is at least partly transferred to the rod displacement feature. Via the dose button, the user may advantageously move the rod displacement feature distally with respect to the cartridge. If the assembly is in the initial state, the user may thus prime the assembly via the dose button. When the assembly is in the primed state, the user may effect a dose setting, a cancelling or decreasing the size of a dose or a dose dispensing of the drug from the drug delivery device via the dose button. The assembly may be configured that for a dose setting, the dose button has to be rotated with respect to the housing while for a dose dispensing, the dose button has to be actuated such as depressed with respect to the housing.

In an embodiment, the assembly comprises a coupling element, wherein a unidirectional coupling is formed between the piston rod and the coupling element. The coupling element is fixed to the housing and arranged and configured such that a proximal movement of the piston rod with respect to the housing is prevented. This embodiment provides the advantage that, a reset of the piston rod and/or a misuse of the drug delivery device is prevented. Furthermore, it may be prevented that any substance can re-enter the cartridge. By this means, safety aspects of the assembly and/or the drug delivery device may be accounted for.

In an embodiment, the assembly is configured such that the user can replace the cartridge and reset the piston rod. This provides the advantage that the drug delivery device can be used for more than one cartridge sequentially.

In an embodiment, in the initial state, an initial content of the drug is retained in the cartridge. The initial content preferably relates to a maximum amount or content of drug which can be retained in the cartridge.

In an embodiment, in the initial state, the distance between a proximal face of piston rod and a distal face of the rod displacement feature is smaller than the distance between the first and the second position. According to this embodiment, it is assured that during movement of the rod displacement feature from the first position to the second position, the piston rod is effectively moved with respect to the cartridge, as the rod displacement feature may then abut the piston rod.

In an embodiment, in the initial state, a distance between the plunger and the piston rod is smaller than a distance between the first position and the second position of the rod displacement feature. The distance may result from manufacturing tolerances. The distance by which the rod displacement feature is moved may compensate manufacturing tolerances. By means of said movement, it may be ensured that the plunger and the piston rod abut in the primed state. According to this embodiment, it is assured as well that during movement of the rod displacement feature from the first position to the second position, the piston rod is effectively moved with respect to the cartridge.

In an embodiment, the plunger and the cartridge are configured such that the initial static friction force takes values between 10 Newtons and 20 Newtons.

In an embodiment, the drive mechanism is configured such that the driving force takes values between 3 Newtons and 10 Newtons.

A further aspect of the present disclosure relates to a method of operating the assembly comprising the steps of providing an assembly in an initial state. The assembly comprises a housing having a proximal end and a distal end, a cartridge, a plunger being movably retained in the cartridge, a piston rod arranged to move the plunger distally with respect to the cartridge and a rod displacement feature being movable between the first and the second position with respect to the housing. The method further comprises moving the rod displacement feature from the first position to the second position with respect to the housing, wherein said movement is transferred to the piston rod such that the piston rod is moved with respect to the cartridge and the assembly is switched from the initial state to the primed state. The method further comprises moving the rod displacement feature from the first position to the second position with respect to the housing, wherein said movement is not transferred to the piston rod. Said movement of the rod displacement feature from the first position to the second preferably occurs every time the dose button is depressed, e.g. to initiate a delivery action.

Features which are described herein above and below in conjunction with different aspects or embodiments may also apply for other aspects and embodiments.

Particularly, features described with respect to the arrangement may apply for the method, the unit and the module and vice versa.

Further features and advantages of the subject matter of this disclosure will become apparent from the following description of the exemplary embodiment in conjunction with the figures, in which:

FIGS. 3a and 3b show a partial perspective view of components of the drug delivery device. FIG. 3a shows a situation in which a clutch mechanism is engaged and FIG. 3b shows a situation in which the clutch mechanism is disengaged.

Like elements, elements of the same kind and identically acting elements may be provided with the same reference numerals in the figures. Additionally, the figures may be not true to scale. Rather, certain features may be depicted in an exaggerated fashion for better illustration of important principles.

Figure 1:
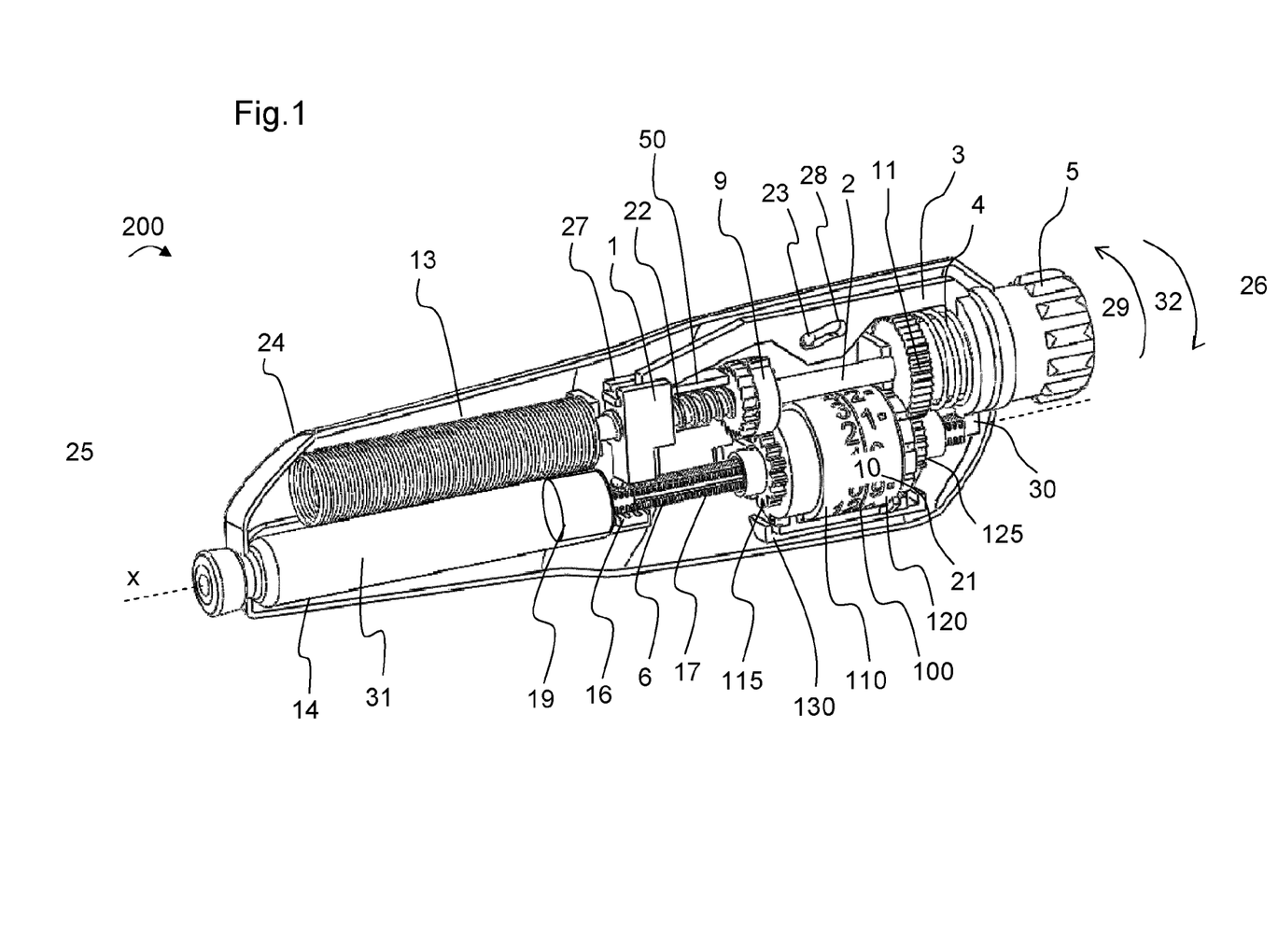
FIG. 1 shows a perspective view of components of a drug delivery device.

FIG. 1 shows a perspective view of a drug delivery device 200. The drug delivery device may be a disposable drug delivery device. The drug delivery device 200 comprises a housing 24 which houses further components. Only one half of the housing 24 is shown in FIG. 1 such that inner components of the drug delivery device 200 are visible. The drug delivery device 200 further comprises a drive member 1 and a piston rod 6. The piston rod may have a cross-section resembling a square, rectangle, parallelogram, circle or ellipse.

The drive member 1 is configured to move the piston rod 6 in a distal direction, e.g. during a dose delivery of the drug delivery device 200. The drug delivery device 200 comprises a longitudinal axis x, a distal end 25 and a proximal end 26. Preferably, the longitudinal axis x extends through the distal end 25 and the proximal end 26. In other words, the distal end 25 and the proximal end 26 may be spaced along the longitudinal axis. The drug delivery device 200 further comprises a, preferably replaceable, cartridge 14 in which a plunger 19 is retained. The piston rod 6 may be arranged next to or abut the plunger 19. The cartridge 14 may further contain a drug 31 or medical substance to be dispensed from the drug delivery device 200. The drug 31 may be dispensed in measured doses. The drug 31 may be retained in the cartridge 14. The cartridge 14 may contain 1.5 ml or 3 ml of the drug 31. Preferably, the cartridge 14 is arranged or aligned longitudinally. The piston rod 6 may also be arranged or retained longitudinally such that it is movable with respect to the cartridge 14. The drug delivery device 200 further comprises a dose member 2 which may effect a dose setting and a dose dispensing of the drug delivery device. The dose member 2 is threadedly engaged with the drive member 1, e.g. via an outer thread 22. Accordingly, the drive member 1 may comprise an inner thread matching with the outer thread 22. Thereby, said threaded engagement may be configured such that during a rotation of the dose member 2 with respect to the housing 24, the drive member 1 is axially moved. In a setting mode of operation, the dose member is rotatable in a first or second direction with respect to the housing to set a dose and in a dispensing mode of operation, the dose member 2 is rotatable in a second direction opposite to the first direction with respect to the housing to dispense a set dose. The drug delivery device 200 further comprises a displacement member 3 which may be configured to displace or to contribute to the displacement of the drive member 1.

The dose member 2 and the displacement member 3 are preferably aligned parallel to the longitudinal axis x but arranged radially offset from the cartridge 14 and the piston rod 6. Drive member 1 may at least partially be arranged between the piston rod 6 and the dose member 2. A longitudinal axis of the drive member may thereby be aligned radially. The dose member 2 and the displacement member 3 may comprise an elongate shape, respectively. The displacement member 3 is engaged to the drive member 1 via a guidance 27 of drive member 1. The guidance 27 may be configured such that, e.g., when the dose member 2 is rotated, the drive member 1 is rotationally locked with respect to the displacement member 3 such that the dose member 2 and the drive member 1 are rotated relative to each other. The drug delivery device 200 further comprises a spring element 4 and a dose button 5. The spring element 4 is retained between a pinion 11 of the dose member 2 and the dose button 5. The displacement member 3 comprises a drive member displacement member 50 which comprises an elongate shape and which is aligned parallel to the longitudinal axis x. The length of the drive member displacement member 50 may relate to the travel of the drive member 1 and in this way to the amount of drug 31 to be dispensed during the dispensing of drug from the filled cartridge. The drive member displacement member 50 is retained by the guidance 27. Preferably, the guidance 27 rotationally and radially locks the drive member displacement member 50, whereby only relative axial movement of said components is allowed.

The displacement member 3 comprises a rod displacement feature 30. In the depicted situation, the drug delivery device 200 is in an initial state. During the first use of the drug delivery device 200, the rod displacement feature 30 may abut the piston rod 6.

The drug delivery device 200 further comprises an indication assembly 100. The indication assembly 100 comprises a first indication member 110 and a second indication member 120. The piston rod 6 extends through the first and the second indication members 110, 120. The indication assembly 100 further comprises a locking member 130 which is configured to rotationally lock the first and the second indication member 110, 120 with respect to the housing 24. The drug delivery device 200 further comprises a guide feature 23 which is fixed to the housing 24. When, e.g. the dose button 5 is moved distally, the displacement member 3 is also moved distally against the resilience of the spring element 4. Thereby, the displacement member 3 is guided by the guide feature 23 which is engaged to a bore 28 of the displacement member 3. Via the bore 28 and the guide feature 23, an axial movement of the displacement member 3 may at least partly be converted into a radial movement of the displacement member 3 and/or the drive member displacement member 50. The displacement member 3 may comprise a certain flexibility.

The drug delivery device 200 further comprises a drive spring 13 which is configured such that it is loaded upon a rotation of the dose member 2 in a first direction (cf. arrow 29). To this effect, a distal end of the drive spring 13 is preferably fixed to the housing 24 and a proximal end of the drive spring 13 is preferably fixed to, e.g. a distal end of the dose member 2. The drive spring 13 is a torsion spring. During setting of a dose of drug 31, the drive spring 13 is loaded and spring energy is stored which can be used for a delivery of the drug 31. The displacement member 3 is rotationally locked with respect to the housing 24. In the setting mode of operation, the dose button 5 is rotated in the first direction 29. The dose button 5 is connected to the dose member 2, wherein said connection is configured such that the dose member 2 is also rotated in the first direction along with the dose button 5, such that the drive spring 13 is loaded. Due to the threaded engagement of the dose member 2 and the drive member 1, in the setting mode of operation, the drive member 1 is moved proximally while in the dispensing mode of operation, the drive member 1 is moved distally. In the setting mode of operation, the dose button 5 may also be rotated in a second direction (cf. arrow 32) opposite to the first direction 29 in order to decrease or cancel a set dose of drug 31. This would move drive member 1 distally. The dose button may be operated, e.g. rotated to dial the size of a dose to be delivered. The size may span a range between zero units and a maximum number of gradations or units, e.g. 120.

The displacement member 3 and the dose member 2 are coupled via a releasable clutch mechanism by which said components are rotationally lockable. The releasable clutch mechanism is configured to withstand the spring force of the drive spring when a dose is set. When a maximum settable dose is set, the releasable clutch mechanism has to withstand a maximum spring force. The releasable clutch mechanism can be released by distal movement or depressing of the dose button 5 with respect to the housing 24. Thereby, the displacement member 3 and the dose member 2 are disengaged (cf. FIG. 3 further below).

The spring element 4 biases the releasable clutch mechanism towards the engaged state. In the setting mode of operation, the drive member is preferably in a first position, wherein it is disengaged from the piston rod 6. When the dose button 5 is depressed or moved distally which is preferably manually performed by a user of the drug delivery device 200, it is preferably switched from the setting mode to the dispensing mode of operation. During distal movement of the dose button 5 and the displacement member 3 with respect to the housing 24, the displacement member 3 is guided via the guide feature 23 in such a manner that the displacement member 3 displaces the drive member 1 radially, i.e. towards the piston rod 6 such that the piston rod 6 is displaced from the first to a second position. In the second position, the drive member 1 is engaged to the piston rod 6. The drive mechanism is preferably configured such that at the same time or slightly after the drive member 1 has engaged the piston rod , the releasable clutch mechanism is released and the spring force of the loaded drive spring 13 drives the dose member 2 such that the dose member 2 is rotated in the second direction 32. The drive spring 13 is preferably configured to provide for a sufficient spring force for a minimum dose of drug 31 to be dispensed from the drug delivery device 200 when the piston rod 6 is in the second position. Due to the threaded interaction of the dose member 2 and the drive member 1, the drive member 1 is moved distally with respect to the piston rod 6 when the dose member 2 rotates. The piston rod 6 comprises a piston rod feature 17 and the drive member 1 comprises a drive feature 15 (cf. FIG. 2). By an engagement of the drive feature 15 with the piston rod feature 17, a distal movement of the drive member 1 may be transferred to the piston rod 6 such that the piston rod 6 is moved distally with respect to the housing 24. Consequently, the plunger 19 is moved distally inside the cartridge 14 in order to dispense drug 31 from the drug delivery device 200. The drug delivery device 200 further comprises a coupling element 16 which is configured such that the piston rod 6 is prevented from being moved in the proximal direction. When the dose button 5 is released either during or after a dispensing operation, the releasable clutch mechanism is reengaged and the drive member 1 is moved back from the second into the first position thus switching the drive mechanism back into the setting mode of operation. The drug delivery device 200 may be an injector-type device comprising a needle or a needle assembly (not explicitly indicated) which may be provided at the distal end 25. Furthermore, the drug delivery device 200 may comprise a cap (not explicitly indicated) to cover the distal end 25. The dose button 5 may need to be rotated six times during setting of a dose. This may correspond to a set dose of 120 units of drug 31 to be dispensed.

In the following, a priming mechanism is described by which the drug delivery device 200 may be switched from an initial state to a primed state. In the initial state, the drug delivery device 200 is preferably in an as-fabricated or as-assembled state, wherein the dose button 5 has not yet been actuated or pressed. Then, the cartridge 14 preferably contains an initial amount of drug 31. The rod displacement feature 30 is axially movable between a first position and a second position. Expediently, the second position is distally offset from the first position. In the initial state, the piston rod 6 and the rod displacement feature 30 are arranged such that some or all of the movement of the rod displacement feature 30 from the first position to the second position is transferred to the piston rod 6 such that the piston rod 6 is moved with respect to the cartridge 14. In the primed state, axial movement of the rod displacement feature 30 from the first position to the second position is not transferred to the piston rod 6. Particularly, when the dose button 5 is in the initial state, a proximal face 47 of the piston rod 6 and a distal face 46 of the rod displacement feature 30 preferably abut (cf. also FIG. 6). Alternatively, the distance between the proximal face 47 of the piston rod 6 and a distal face 46 of the rod displacement feature 30 is at least smaller than the distance between the first and the second position. When, in the initial state, the dose button 5 is pressed by the user for the first time, the rod displacement member 30 is moved axially, thereby moving or advancing the piston rod 6 distally with respect to the cartridge 14. Expediently, a needle is provided which in turn provides fluid communication between the interior of the cartridge 14 and the outside. The dose button 5 is moved until the rod displacement feature 30 is arranged in the second position, whereby an initial static friction force between the plunger 19 and the cartridge 14 is overcome. Thereby, the drug delivery device 200 is primed. The priming operation may additionally comprise the removal of clearances and/or tolerances and the application of compression or tension to further device components such that the device is prepared for an operation with no or only a minimum play between elements of the drive mechanism. The use of force transferred from the rod displacement member 30 to the piston rod 6 may help the drive mechanism to overcome initial static friction forces, particularly between the plunger 19 and the cartridge 14.

In the primed state, the driving force is preferably sufficient to move or advance the piston 19 distally with respect to the cartridge 14. As an advantage, the drive spring 13 may be designed smaller and more efficient with respect to costs and space requirements. In the initial state, the distance between the piston rod 6 and the rod displacement feature 30 is preferably greater than a manufacturing tolerance of the cartridge 14 and/or the piston rod 14. Thereby, it is assured, that the direct distal movement of the rod displacement feature—which is effected manually by the user—is effectively transferred to the piston rod 6. Preferably, the plunger 19 and the cartridge 14 are configured such that the initial static friction force takes values between 10 N and 20 N. Preferably, the mentioned drive mechanism is configured such that the driving force takes values between 3 N and 10 N.

The distance by which the dose button 5 is depressed may be 3 to 4 mm. The rod displacement feature 30 may be moved axially between the first and the second position. The distance the rod displacement feature 30 is moved axially may be 2 mm. Additionally, there may be a play or clearance of distance B of 1 to 2 mm between the dose button 5 and the displacement member 3 (cf. FIG. 6). To this effect, a further biasing member (not explicitly indicated) may be provisioned which tends to separate the mentioned components accordingly.

An advantage of the described priming functionality pertains to the effect that once the drug delivery device 200 is primed, the user may repeat the actuation or depressing of the dose button 5 if he is not sure about the state of the device. By means of the force necessary to depress the dose button 5, the user will immediately realize whether the device has already been primed or not. Thereby, it is contributed to a simple and safe operation of the drug delivery device 200. The presented drug delivery device 200 provides the advantages of, for instance, a comfortable, user-friendly shape, a low injection force owing to the priming mechanism, semi-automatic injection and the possibility to assemble the drug delivery device in an easy way. Moreover, the drug delivery device may be easily distinguished from other devices due to its characteristic shape. That is to say, the shape of the drug delivery device may deviate slightly from a cylinder-like shape which is usual for similar drug delivery devices. To this effect, it may be easier to hold it in the palm of the user's hand and/or to operate the drug delivery device.

Figure 2A:
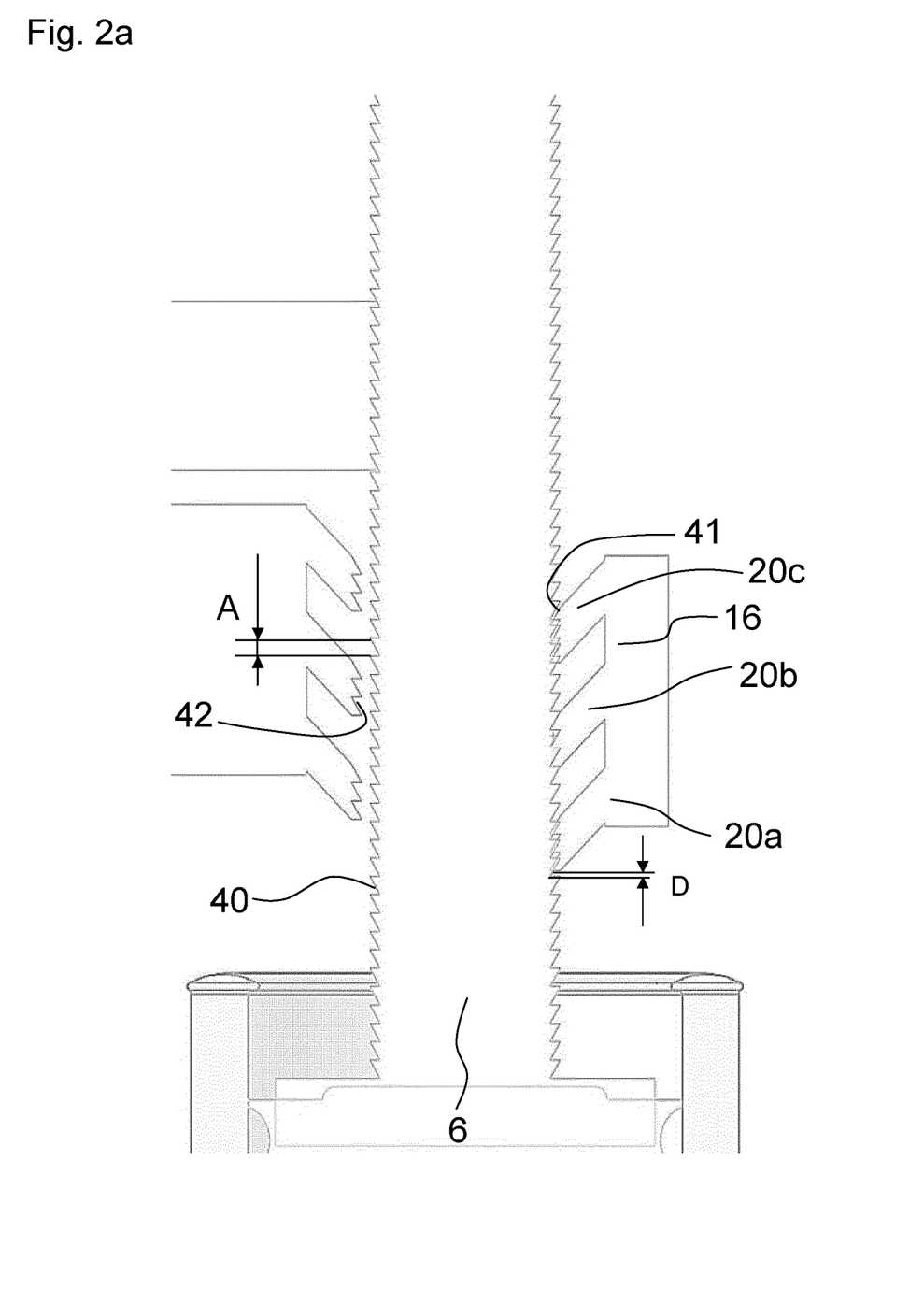
FIGS. 2a to 2c show the schematics of a side view of components of a drive mechanism for a drug delivery device.
Figure 2B:
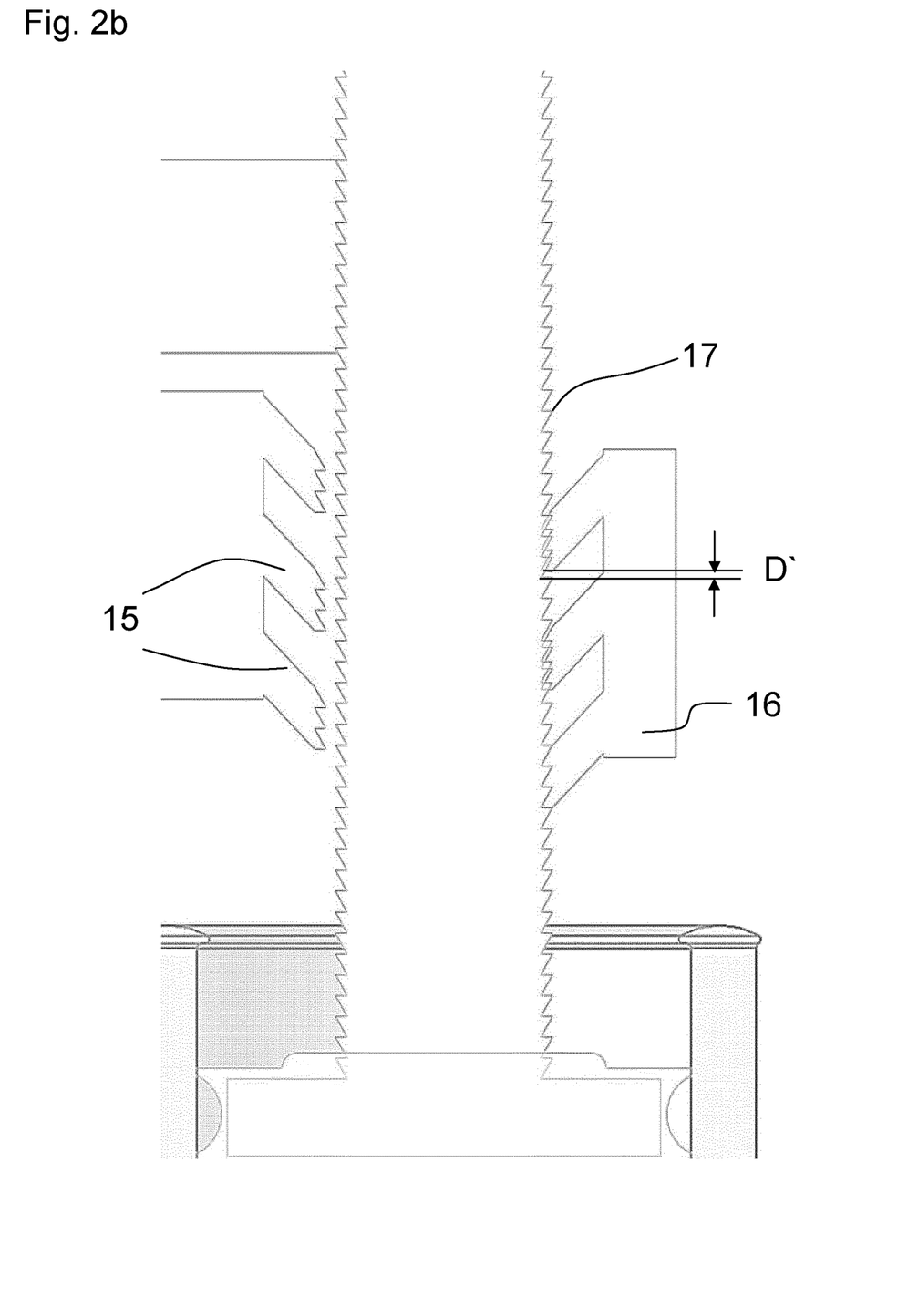
Figure 2C:
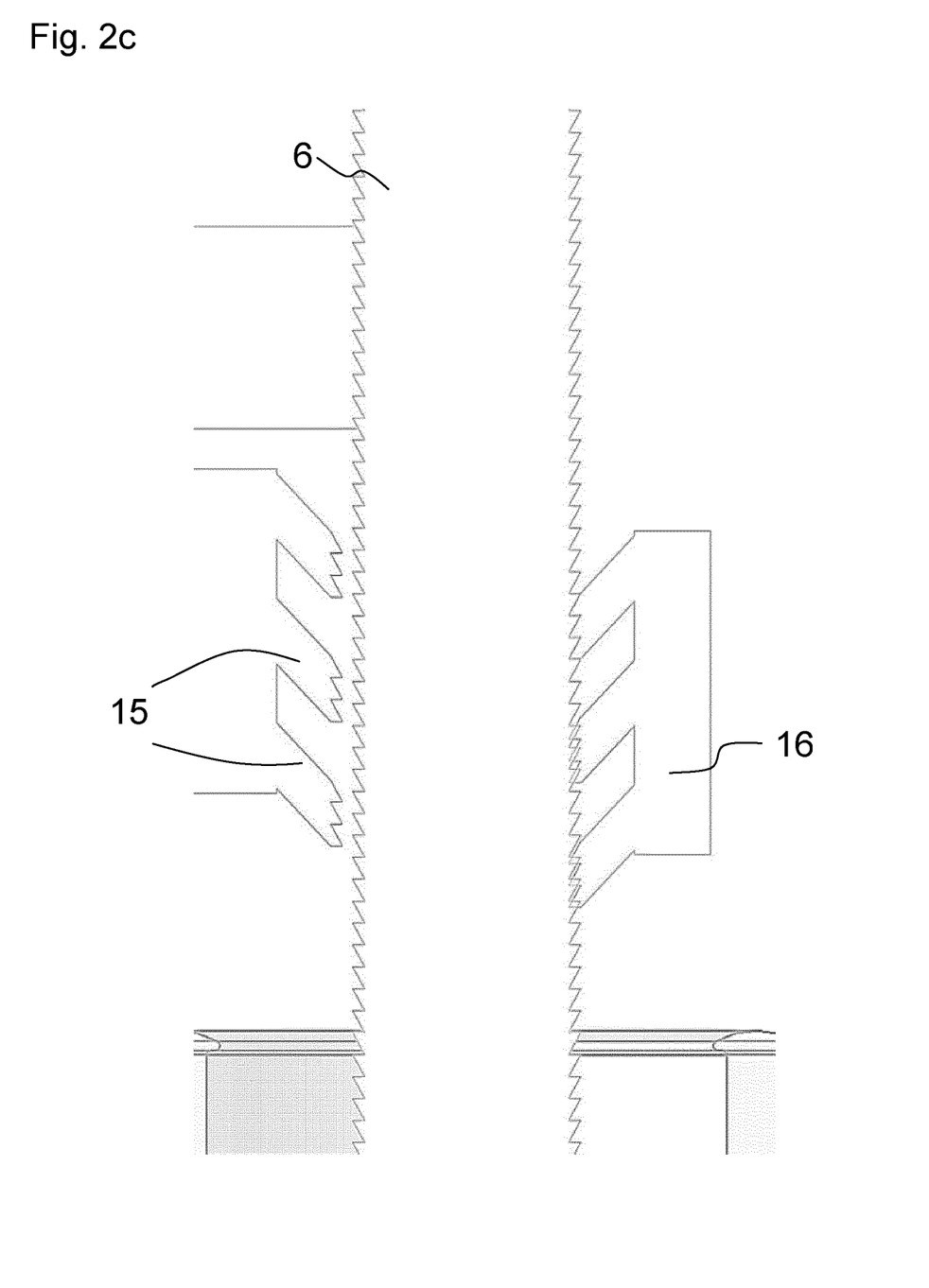

FIG. 2 illustrates a coupling between the piston rod 6 and the coupling element 16 by means of the FIGS. 2a to 2c. Drive feature 15 of the drive member 2 may constitute a plurality of drive features 15 which are shown each with a tilt towards the distal end 25. The depicted situation respectively relates to the setting mode of operation, wherein the drive features 15 are disengaged from the piston rod 6. The coupling element 16 is preferably fixed to or integrally formed with the housing 24. The coupling element 16 comprises three axially spaced coupling features 20 each of which comprises teeth 41. The coupling features 20 are also tilted towards the distal end 25. The piston rod 6 comprises a set of teeth 40 which exhibit the piston rod feature 17. The teeth 40 are configured uniformly and arranged equidistantly. Furthermore, the teeth 40 may be arranged at an inwardly directed, as well as an outwardly directed side surface of the piston rod 6. The side surfaces of the piston rod 6 may be flat or non-flat, such as even. Each of the coupling features 20 is configured to establish a unidirectional coupling with the teeth 40 such that a proximal movement of the piston rod 6 with respect to the housing 24 is prevented. In FIG. 2a, only the coupling feature 20b in the middle establishes said unidirectional coupling, as proximal end faces of the teeth 40 abut distal end faces of teeth 41 of that coupling element while this is not the case for the other coupling features 20b, c. The distance between the proximal end faces of two adjacent teeth 40 of the piston rod 6 is indicated by A. The axial distance between the coupling features 20 is chosen such that the distance D between a distal end face of a tooth 41 of the coupling feature 20c which does not establish the unidirectional coupling and a proximal end face of a tooth 40 of the piston rod 6 feature is smaller than the distance A. Preferably, the distance D corresponds to a minimum amount of a drug 31 to be dispensed from the delivery device 200. The distance D is preferably defined by those teeth 42 of the piston rod 6 which are arranged proximally next to the respective tooth 41 of the respective coupling element. The distance D corresponding to a minimum amount of a drug 31 to be dispensed is expediently smaller than the distance A. Consequently, the piston rod 6 may be moved distally with respect to the coupling element 16 by a distance smaller than the distance A. In FIG. 2b, as compared to the FIG. 2a, the piston rod 6 has been moved distally (to the left) with respect to the coupling element 16 by the distance D. Thereby, the proximal end faces of the teeth 40 of the piston rod 6 have been moved out of abutment with the distal end faces of the teeth 41 of the middle coupling feature 20b and proximal end faces of the teeth 40 abut distal end faces of the left coupling feature 20a such that only this coupling feature establishes unidirectional coupling to the piston rod 6. In FIG. 2c, the piston rod 6 has been moved further axially by the distance D', as compared to FIG. 2b. As a consequence, only the right coupling feature 20c forms the mentioned unidirectional coupling to the piston rod 6. The distance D' may relate to the distance D.

The drive features 15 of the drive member 1 are axially spaced, wherein each drive feature 15 comprises teeth 42 being configured to be engagable with the teeth 40 of the piston rod 6, wherein the drive features 15 and the teeth 42 are configured such that when the drive member 2 is in the second position, a distal end faces of a teeth 42 of one of the drive features 15 abut proximal end faces of teeth 40 of the piston rod 6 and distal end faces of a teeth 42 of another drive feature 15 are spaced preferably by the distance D from proximal end faces of a teeth 40 of the piston 6.

The functionality which is described herein by means of three teeth 41 may also function with coupling features and drive features which only comprise one tooth each. However, the provision of a plurality of teeth adds greater strength and some redundancy in the case of failure.

Figure 3A:
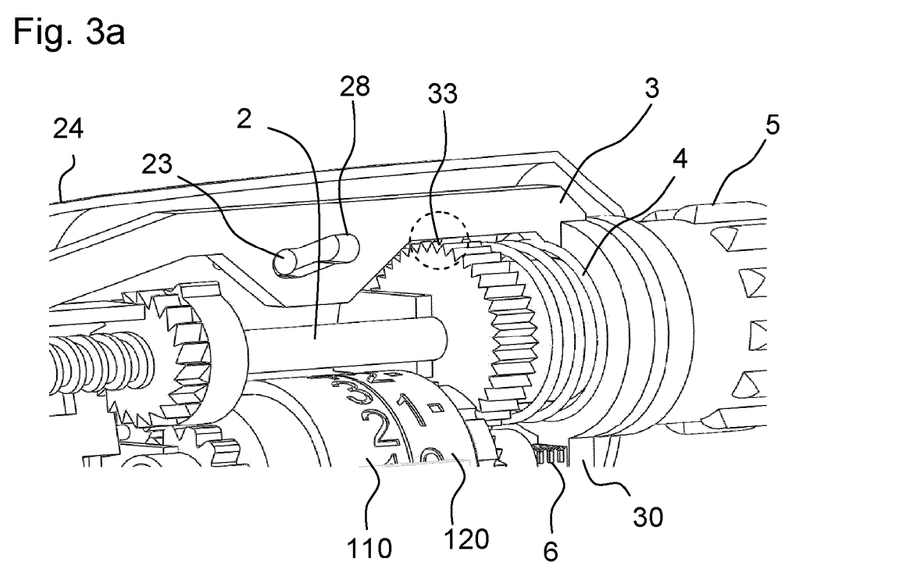
Figure 3B:
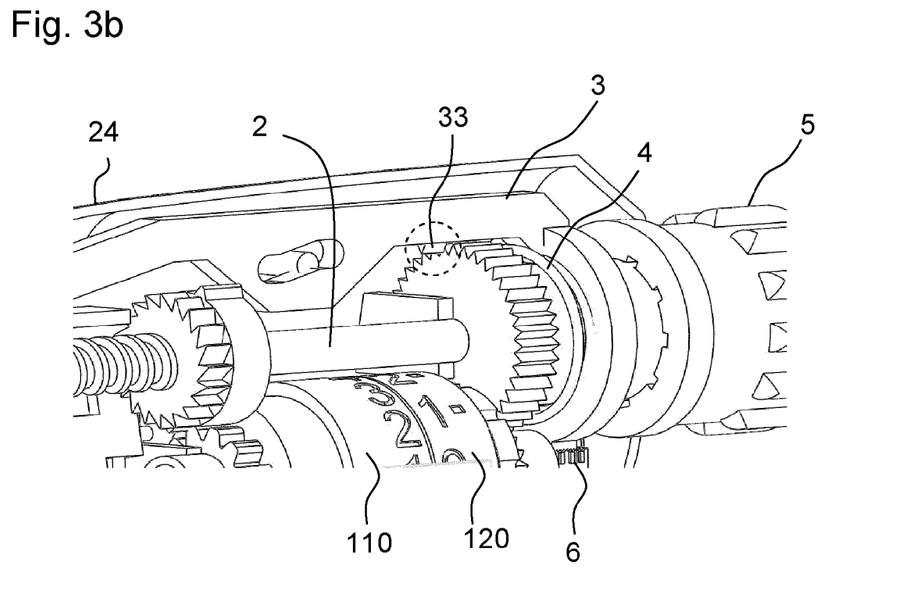

FIG. 3a shows a partial perspective view of inner components of the drug delivery device 200 in the setting mode of operation. The displacement member 3 comprises a clutch feature 33 which is, in the depicted situation, engaged to the pinion 11 of the dose member 2. In this situation, the releasable clutch mechanism is engaged. The pinion comprises teeth 48. The clutch feature 33 is a tooth-like clutch feature which is engaged or splined to the teeth 48 (cf. dashed circle). Although the dose member 2 may be selectively rotationally locked with respect to the housing 24 against the spring force of the drive spring 13, it may still be rotated, e.g. by a rotation of the dose button 5 with respect to the housing 24 which is performed by the user. During a setting operation, particularly during a clockwise rotation (cf. arrow 29 in FIG. 1) of the dose member 2 with respect to the displacement member 3, said clutch interaction between the clutch feature 33 and the pinion 11 may be overcome by the user. The torque required to set a dose may be 13.4 mNm for a set dose of zero and 25.4 mNm for a set dose of 120 units. The torque required to decrease or cancel a dose may be 16.8 mNm for a minimum dose and 4.8 mNm for the maximum settable dose. Expediently, said torques are larger than the torque which is applied to the dose member 2 by the drive spring 13. FIG. 3b shows the situation in the dispensing mode of operation, wherein the clutch feature 33 has been disengaged from the teeth 48 of the pinion 11, by movement of the dose button 5 with respect to the housing 24. As compared to FIG. 3a, also the displacement member 3 has been moved distally with respect to the dose member 2. Consequently, in FIG. 3b, the dose member 2 is free to rotate with respect to the displacement member 3. In this situation, it is enabled that the drive spring 13 drives the dose member 2 in the second direction or counter clockwise (cf. arrow 32 in FIG. 1) by rotation.

Figure 4:
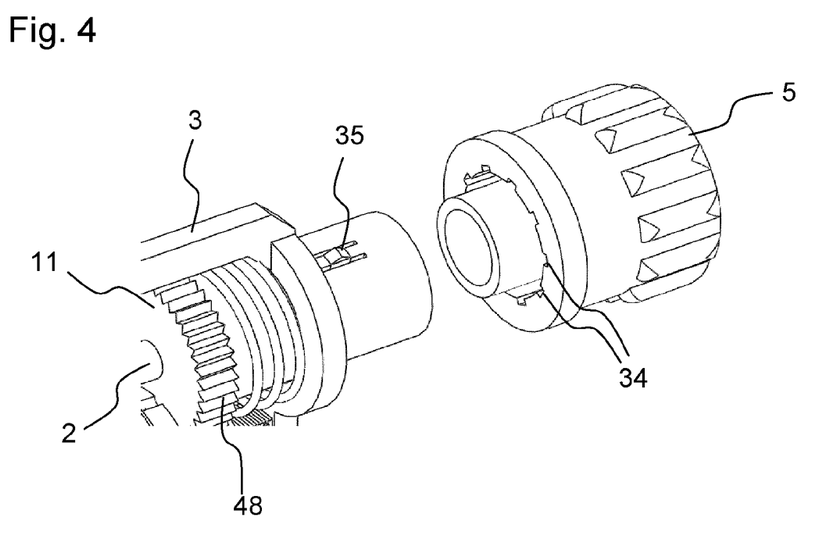
FIG. 4 shows a perspective view of components of the drug delivery device.

FIG. 4 shows parts of components of the drug delivery device 200 near the proximal end 26. In the setting mode of operation, the dose button 5 is rotationally locked to the dose member 2 by a dose member spline 35 which is retained in a recess 34 of the dose button 5 such that the dose member 2 is rotated along with the dose button 5. In the dispensing mode of operation, the dose member 2 is free to rotate with respect to the dose button 5. To this effect, the dose member spline 35 and the recesses 34 are configured such that when the dose button 5 is moved distally with respect to the dose member 2, e.g. during a dispensing operation, the dose member spline 35 is disengaged from the corresponding recess 34 and the dose member 2 is free to rotate with respect to the dose button 5. When the dose button 5 is released again, e.g. during or after a dispensing operation, the dose member spline 35 is reengaged to one of the recesses 34, e.g. to that recess which is arranged closest to the dose member spline 35. This is due to the effect of the spring element 4 which biases the dose member 2 towards the distal end 25.

Figure 5:
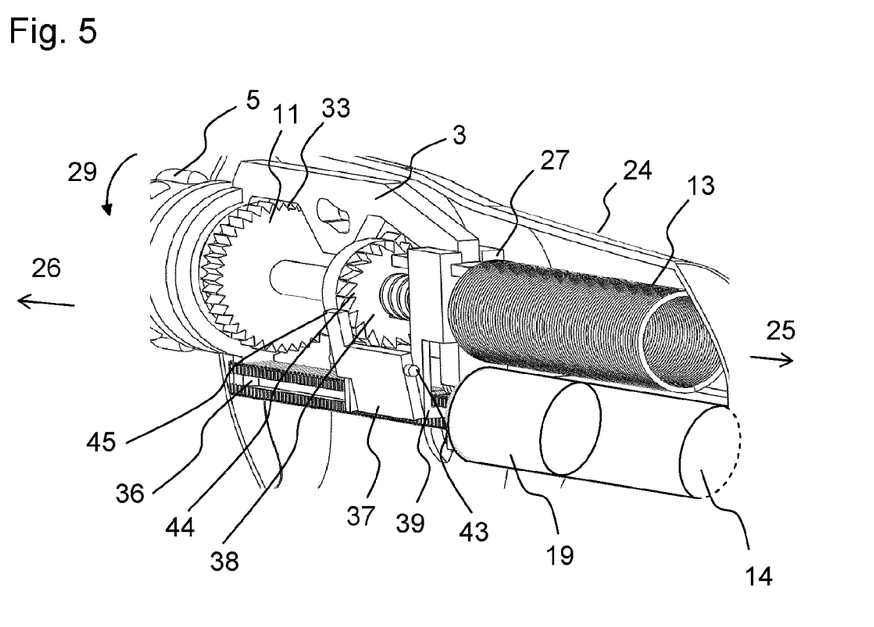
FIG. 5 shows a perspective view of further components of the drug delivery device.

FIG. 5 shows a perspective view of components of the drug delivery device 200 illustrating, e.g. the function of a last dose mechanism of the drug delivery device 200. A last dose ratchet 37 is provisioned to hinder, e.g. a user to set a further dose when the maximum settable dose is already reached or set. When a dose of a drug 31 is set, the drive member 1 moves away from the distal end 25. When a dose is dispensed, the piston rod 6 moves distally with respect to the housing 24 together with the drive member 1. The drive member 1 comprises a drive member arm 39. The last dose ratchet 37 may be borne or retained by the pins 43 which may interact with a further component of the drug delivery device 200 or the housing 24 such that the last dose ratchet 37 is rotated around an axis defined by the pins 43. The dose member 2 comprises a dose member ratchet 38 further comprising teeth 44 which are disposed on a circumferential face or another face. When a large or a maximum number of units has already been dispensed from the drug delivery device 200 and/or when a large or a maximum dose is set, the drive member arm 39 engages a ramp 36 near the proximal end 26. Thereby, the drive member arm 39 is moved radially outwards, thus rotating the last dose ratchet 37 around the axis which extends through the pins 43. Due to the rotation of the last dose ratchet 37, an end portion 45 of the last dose ratchet 37 engages the teeth 44 of the dose member ratchet 38 such that the dose member 2 is prevented from rotation in the first direction 29, i.e. the direction in which the set dose is increased. In the setting mode of operation, the dose member 2 may then be moved in the second direction (cf. arrow 32 in FIG. 1) in order to decrease or cancel the dose. Thereby, the drive member 1 is moved distally with respect to the piston rod 6. When the maximum dose is set, the dose member 2 is thus prevented from being rotated in the first direction 29 to set an additional dose of drug 31.

Figure 6:
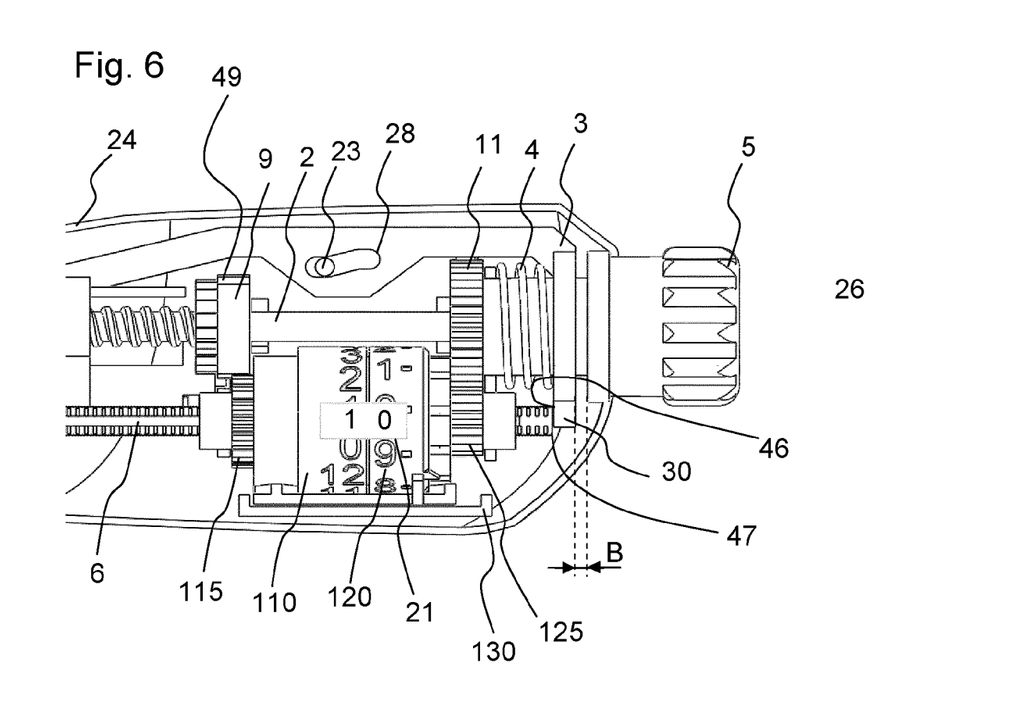
FIG. 6 shows a side view of components of the drug delivery device.
Figure 7:
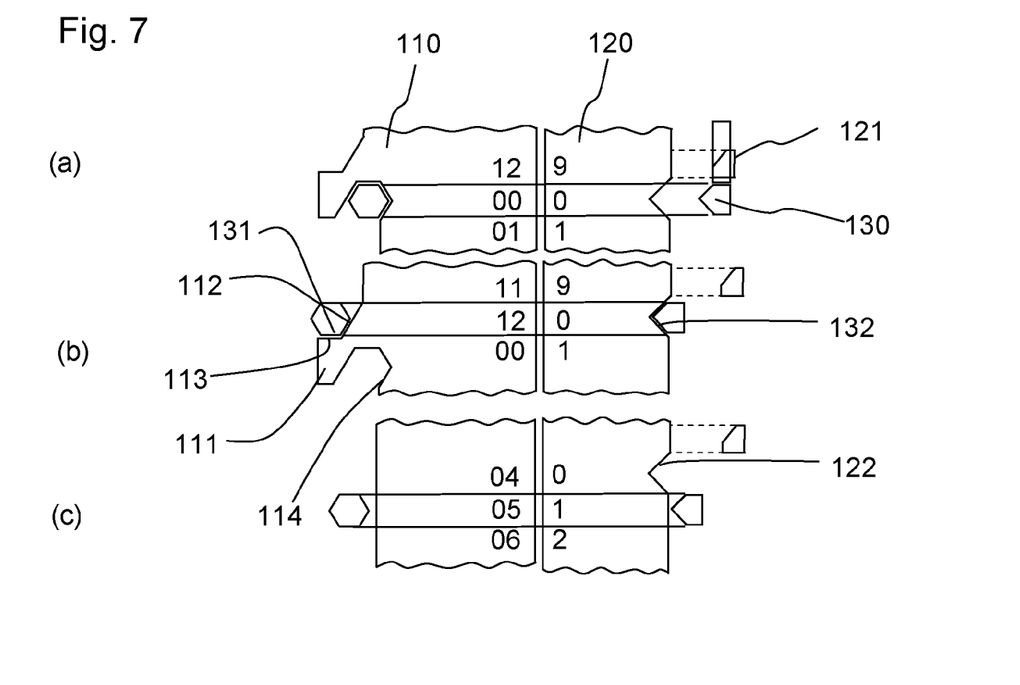
FIGS. 7A to 7C show the schematics of an indication mechanism of the drug delivery device, respectively.

FIG. 6 shows a partial side view of inner components of the drug delivery device 200. In the depicted situation, the drug delivery device 200 is in an initial state and the rod displacement feature 30 abuts or is closely arranged to the piston rod 6. When the dose button 5 is then moved or depressed in the distal direction by a distance B which may correspond to 1 mm, the dose button abuts the displacement member 3. Upon further distal movement of the dose button 5, the displacement member 3 and also the piston rod 6 is moved distally against the resilience of the spring element 4. The indication assembly 100 is shown in FIG. 6 in greater detail. The drug delivery device 200 may comprise a window 21 which may be comprised by the housing 24. The dose member 2 comprises a first pinion 9. The pinion 11 exhibits a second pinion, as mentioned above. The first indication member 110 further comprises a first corresponding pinion 115 which is engaged or engagable to the first pinion 9. The first pinion 9 comprises a protrusion 49. The second indication member 120 further comprises a second corresponding pinion 125 which is engaged to the second pinion 11. The first and the second indication member 110, 120 comprise indication numbers or symbols which, e.g. to indicate the size of a set dose. The first and the second indication members 110, 120 are mechanically decoupled from one another. The dose member 2 may be suitable to drive the first and the second indication member 110, 120, particularly to rotate said components via the first and the second pinion 9, 11 with respect to the housing 24. The first indication member 110 may be incrementally rotatable such that when the dose member 2 is rotated by one revolution, the first indication member 110 is rotated by one increment due to an engagement of the protrusion 49 with the first corresponding pinion 115. The locking member 130 may be rotationally locked with respect to the housing 24 of the drug delivery device 200. Thereby, the housing 24 may be and/or act as a locking member guide. The first and the second indication members 110, 120 are rotatable with respect to the locking member 130. The axis of rotation may be an axis parallel to the longitudinal axis x of the drug delivery device 200. The locking member 130 may be axially movable respect to the housing 24. In FIG. 6, a rotation of the dose member 2 in the first direction would lead to a rotation of the second indication member 120 in the second direction such that the number 1 would be indicated through the window 21. In FIG. 7 the counting direction of the depicted numbers of the first and second indication member 110, 120 is reversed for the sake of clarity.

By means of FIG. 7 the indication assembly 100 is described schematically and in greater detail. The indication assembly 100 may contribute to a display mechanism of the drug delivery device 200 which allows, e.g. for an indication and/or counting of set doses of the drug delivery device 200. The first indication member 110 comprises a first indication feature 111 and the second indication member 120 comprises a second indication feature 122 which may be a recess. The first indication feature 111 comprises a guiding surface 112 and a stop face 113. The locking member 130 comprises a first locking member feature 131 and a second locking member 132. The first indication member 110 further comprises a cut-out 114. The first and the second locking member feature 131, 132 are arranged on opposite sides of the locking member 130. The first and the second indication member 110, 120 are at least partially arranged axially between the first and the second locking member feature 131, 132.

In FIG. 7a, a dose of zero units is indicated. The locking member 130 is arranged in the cut-out 114. Via the cut-out the first indication member 110 is rotationally locked in the second direction with respect to the locking member 130.

The second indication member 120 further comprises a second interaction feature or stop 121. The locking member 130 is arranged at an axial position, wherein it abuts the stop 121, thereby simultaneously locking the second indication member 120 rotationally in the second direction with respect to the locking member 130. This situation may correspond to an initial position of the locking member 130, wherein the set dose is zero. The first and the second indication member 110, 120 may comprise cylindrical indication surfaces. The first and the second locking member features 131, 132 comprise one or more even surfaces which are arranged obliquely with respect to the axis of rotation of the first or the second indication member 110, 120. The first and the second indication member 110, 120 may rotate around a common axis, preferably around the longitudinal axis x. When a dose of the drug delivery device 200 is set, the dose member 2 is rotated in the first direction via the dose button 5 such that this set dose may be indicated through the window 21. Such rotation may relate to a rotation of the first and the second indication member 110, 120 in a first rotational direction with respect to the locking member 130. A rotation of the dose member 2 in the second direction relates, accordingly, to a rotation of the first and the second indication member 110, 120 in a second rotational direction with respect to the locking member 130. When a dose of the drug delivery device 200 is set, the second pinion 11, drives the second corresponding pinion 125 of the second indication member 120 such that the set dose, i.e. the dose indicated by the indication assembly 100 increases. Thus, when, in FIG. 7, the indicated dose (which may correspond to the number in the middle) is increased, the indication assembly 100 and the dose member 2 are configured such that, when the second indication member 120 is rotated for one revolution, the first indication member 110 is rotated by an angle corresponding to one digit such that "1" is indicated instead of "0". Thereby, the locking member 130 is moved axially and out of the cut-out 114 of the first indication member 110. Now the locking member 130 is in a non-locking position, as, for example, shown in FIG. 7c by means of the indicated dose of 51 units. The locking member 130 is biased towards said non-locking position by a biasing member (not explicitly indicated) with respect to the first and the second indication members 110, 120. Preferably, the locking member is biased towards the initial position of the locking member 130. When the maximum dose of, for example 120 units, is set (cf. FIG. 7b), which may correspond to a predetermined angle of the first and/or the second indication member 110, 120 with respect to the locking member 130, the first locking member feature 131 interacts with the first interaction feature 111 such that the locking member 130 is displaced into a locking position (cf. FIG. 7b) with respect to the indication member 130, thereby rotationally locking the first and the second indication member 110, 120 with respect to the locking member 130 in the first direction. The displacement of the locking member 130 with respect to the first and the second indication member 110, 120 is an axial displacement, e.g. along the longitudinal axis x of the drug delivery device 200 (cf. FIG. 1). In the second direction, the first and the second indication member 110, 120 are still rotatable with respect to the locking member 130. The rotation in the second direction may relate to an operation of the drug delivery device 200, wherein a dose is decreased or cancelled. The axial displacement of the locking member 130 is guided by the guiding surface 112 such that the second locking member feature 132 is axially displaced into the second indication feature 122. In FIG. 7b, the locking member 130 abuts the stop face 113. Now, the first and the second indication member 110, 120 are rotationally locked in the first direction with respect to the locking member 130. This situation may relate to an indication of the maximum settable dose (cf. "120" in FIG. 7b).

As an advantage of the presented indication assembly, a display or indication mechanism for the drug delivery device can be provided which functions with a low number mutually interacting components and thus the counting assembly can be embodied robust and safe.

An application of the presented indication assembly is not restricted to drug delivery device, but merely illustrated exemplarily by that means.

The end of a dose delivery action may be indicated by a feature (not explicitly indicated) which provides an audible feedback when further components of the drug delivery device move relative to one another.

The drug delivery device may additionally comprise components which are not explicitly indicated and/or the function of which is not described herein. For instance, the presented device may comprise a mechanism which decouples or ratchets the dose button relative to the dose member if an excessive torque is applied to the dose button by the user in the setting mode of operation.

Although this is not explicitly described herein, the actuation member and the displacement member may be embodied in a single component and the whole configuration of the drive mechanism and/or the device may be adjusted accordingly.

A further variant of the design may allow the user to decouple the coupling feature from the piston rod feature such that the piston rod can be moved axially, e.g. proximally, with respect to the housing. This is particularly advantageous when the drug delivery device is configured reusable such that the piston rod can be reset and the cartridge can be changed.

The drive mechanism may further comprise a clutch element which is configured to receive motion of the actuation member when the user attempts to set a dose greater than the maximum settable dose. This may be embodied by means of a torque limiter comprising, e.g. protrusions, recesses and/or resilient elements preventing destruction or damage of components of the drive mechanism and/or the drug delivery device when the user attempts to set a dose greater than the maximum settable dose.

The term "drug" or "substance", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
   des Pro36 [Met(O)14 Trp(02)25, Asp28] Exendin-4(1-39),
   des Pro36 [Met(O)14 Trp(02)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropin (Follitropin, Lutropin, Choriongonadotropin, Menotropin), Somatropin (Somatropin), Desmopressin, Terlipressin, Gonadorelin, Triptorelin, Leuprorelin, Buserelin, Nafarelin, Goserelin.

A polysaccharide is for example a glucosaminoglycan, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Drive member
2 Dose member
3 Displacement member
4 Spring element
5 Dose button
6 Piston rod
9 First pinion
11 Second pinion
13 Drive spring
14 Cartridge
15 Drive feature
16 Coupling element
17 Piston rod feature
19 Plunger
20 Coupling feature
21 Window
22 Outer thread
23 Guide feature
24 Housing
25 Distal end
26 Proximal end
27 Guidance
28 Bore
29 First direction
30 Rod displacement feature
31 Drug
32 Second direction
33 Clutch feature
34 Recess (dose button)
35 Dose member spline
36 Ramp
37 Last dose ratchet
38 Dose member ratchet 39 Drive member arm
40 Teeth (piston rod)
41 Teeth (coupling element)
42 Teeth (drive feature)
43 Pin
44 Teeth (dose member ratchet)
45 End portion
46 Distal face
47 Proximal face
48 Teeth (second pinion)
49 Protrusion
50 Drive member displacement member
100 Indication assembly
110 First indication member
111 First interaction feature
112 Guiding surface
113 Stop face
114 Cut-out
115 First corresponding pinion
120 Second indication member
121 Second interaction feature
122 Second indication feature/recess
125 Second corresponding pinion
130 Locking member
131 First locking member feature
132 Second locking member feature
200 Drug delivery device
x Longitudinal axis
A,B,D Distance

The invention claimed is:

1. An assembly for a drug delivery device, the assembly comprising:
a housing having a proximal end and a distal end,
a cartridge, a plunger being movably retained in the cartridge,
a piston rod arranged to move the plunger distally with respect to the cartridge, and
a rod displacement feature movable between first and second positions with respect to the housing, wherein the assembly is configured such that, in an initial state of the assembly, the piston rod and the rod displacement feature are arranged such that movement of the rod displacement feature from the first position to the second position is transferred to the piston rod such that the piston rod is moved with respect to the cartridge and the assembly is switched from the initial state to a primed state and wherein, in the primed state, movement of the rod displacement feature from the first position to the second position is not transferred to the piston rod.

2. The assembly according to claim 1, wherein, when the assembly is switched from the initial state to the primed state, the plunger is moved with respect to the cartridge and an initial static friction force between the plunger and the cartridge is overcome.

3. The assembly according to claim 2, wherein the plunger and the cartridge are configured such that the initial static friction force is between 10 N and 20 N.

4. The assembly according to claim 2, comprising a drive mechanism being configured to transfer a driving force to the piston rod in the primed state.

5. The assembly according to claim 4, wherein the drive mechanism is configured such that the driving force is between 3 N and 10 N.

6. The assembly according to claim 4, wherein the initial static friction force is greater than the driving force.

7. The assembly according to claim 4, wherein the rod displacement feature comprises a displacement member of the drive mechanism, wherein the displacement member is movable to selectively couple a drive member to the piston rod in order to transfer the driving force to the piston rod.

8. The assembly according to claim 7, comprising a drive spring being arranged and configured to drive the movement of the piston rod via the drive member by a driving force generated by a drive spring, whereby the driving force is exerted on the piston rod.

9. The assembly according to claim 1, comprising a spring element which is arranged and configured such that movement of the rod displacement feature from the first position to the second position loads the spring element and the spring force of the spring element moves the rod displacement feature back into the first position.

10. The assembly according to claim 1, comprising a dose button, the dose button being arranged and configured such that movement of the dose button with respect to the housing initiates a delivery of a dose of a drug, wherein the movement of the dose button is at least partly transferred to the rod displacement feature.

11. The assembly according to claim 1, comprising a coupling element, wherein a uni-directional coupling is formed between the piston rod and the coupling element and wherein the coupling element is fixed to the housing and arranged and configured such that a proximal movement of the piston rod with respect to the housing is prevented.

12. The assembly according to claim 1, wherein, in the initial state, an initial content of a drug is retained in the cartridge.

13. The assembly according to claim 1, wherein in the initial state, the distance between a proximal face of the piston rod and a distal face of the rod displacement feature is smaller than the distance between the first position and the second position.

14. The assembly according to claim 1, wherein, in the initial state, a distance between the plunger and the piston rod is smaller than a distance between the first position and the second position of the rod displacement feature.

15. The assembly according to claim 1, wherein the direction of movement of the rod displacement feature from the first position to the second position is the distal direction.

16. A method of operating a drug delivery device comprising the steps of:
moving a rod displacement feature of the drug delivery device from a first position to the second position with respect to a housing of the drug delivery device, wherein said movement is transferred to a piston rod such that the piston rod is moved with respect to a cartridge disposed in the housing and the assembly is switched from the initial state to a primed state; and
moving the rod displacement feature from the first position to a second position with respect to the housing, wherein said movement is not transferred to the piston rod.

* * * * *